United States Patent [19]
Bucalo

[11] 3,982,537
[45] Sept. 28, 1976

[54] DYNAMIC IMPLANTS AND METHOD FOR IMPLANTING THE SAME

[76] Inventor: Louis Bucalo, 155 Roberts St., Holbrook, N.Y. 11741

[22] Filed: Dec. 30, 1974

[21] Appl. No.: 537,572

[52] U.S. Cl. .............................. 128/260; 128/235; 128/261; 424/19; 128/272
[51] Int. Cl.² ................... A61M 1/00; A61M 31/00
[58] Field of Search ............... 128/260, 235, 335.5, 128/261, 272; 424/19, 27, 28; 102/92, 92.6

[56] References Cited
UNITED STATES PATENTS

| 693,329 | 2/1902 | Neubauer | 102/92.6 |
|---|---|---|---|
| 2,640,801 | 6/1953 | Burkhart | 128/261 |
| 3,632,754 | 1/1972 | Balassa | 424/180 |
| 3,773,919 | 11/1973 | Boswell | 424/19 |
| 3,822,702 | 7/1974 | Bolduc | 128/235 |
| 3,867,190 | 2/1975 | Schmitt et al. | 128/335.5 |
| 3,875,300 | 4/1975 | Homm | 424/28 |

*Primary Examiner*—Aldrich F. Medbery
*Attorney, Agent, or Firm*—Steinberg and Blake

[57] ABSTRACT

Dynamic implants adapted to be implanted in the interior tissue of a subject such as a human being, animal, or the like, the dynamic implant being capable of changing the condition of the subject while acting through the tissue and having such properties as being capable of gradual absorption by the tissue. An absorbable type of implant can have dispersed therethrough an agent such as an antibiotic agent, a drug, or the like, so that the latter agent is released continuously while the absorbable substance which forms the implant becomes gradually absorbed by the tissue.

6 Claims, 5 Drawing Figures

DYNAMIC IMPLANTS AND METHOD FOR IMPLANTING THE SAME

BACKGROUND OF THE INVENTION

The present invention relates to implants and implanting methods adapted for use with subjects such as human beings, animals, or the like.

Thus, while the present invention is particularly designed for use with human beings and other mammals, it is also possible to visualize situations where the present invention may have utility with birds, fish, reptiles, etc.

One of the problems encountered with subjects of this type is the problem of administering to such a subject medicinal agents such as antibiotics, drugs, and the like, in a predetermined dosage and over a relatively long interval. At the present time, considerable inconvenience and disadvantages are involved in administrating such agents. For example such agents may be taken orally or they may be injected into the body, but such oral administration and injections must be repeated from time to time, and initially when such agents are administered in such conventional manners the subject receives a relatively large concentrated dose which gradually disappears until another large dose is administered to again undesirably raise the level at which the medicinal agent is received by the body, with the rate of administering the agent to the body gradually diminishing until the next injection or oral administration.

A further problem encountered with subjects of the above type is in connection with localizing the administering of the required agent in such a way that the desired agent will be surely received by the part of the subject requiring the agent. At the present time certain medicinal agents are distributed throughout the entire body although it is only required that they be received by a particular part of the subject.

SUMMARY OF THE INVENTION

It is accordingly a primary object of the present invention to provide a method and structure for avoiding the above drawbacks.

In particular, it is an object of the present invention to provide for subjects of the above type an implant which is capable of being absorbed by the tissue of the subject.

Furthermore, it is an object of the present invention to provide an implant of this type which is capable of releasing to the tissue, while the absorbable substance gradually disappears, agents which will change the condition of the subject.

Furthermore, it is an object of the present invention to provide an implant capable of releasing an agent in a localized manner according to which the agent will reliably be received by a part of the body for which it is intended without necessitating general administration of such an agent throughout the body.

Furthermore, it is an object of the present invention to provide implants of the above type which are capable of being packaged and sold in such a way that they are convenient to use and will have a long shelf life.

According to the method of the invention, the subject has implanted in interior tissue of the subject an implant means which acts dynamically through tissue in which it is implanted for changing the condition of the subject. The implant means of the inventions is dynamic in the sense that it does not take the form of a fixed unchanging structure. Thus, the implant means of the invention includes a substance which is gradually absorbed so that eventually it will disappear, or the implant may take the form of a structure which is capable of having its configuration changed in the tissue so that, for example, muscular characteristics can be provided with the implant of the invention.

Thus, the implant of the invention includes a means for acting dynamically through body tissue in order to change the condition of a subject.

BRIEF DESCRIPTION OF DRAWINGS

The invention is illustrated by way of example in the accompanying drawings which form part of this application and in which.

DESCRIPTION OF PREFERRED EMBODIMENTS

Figure 4:
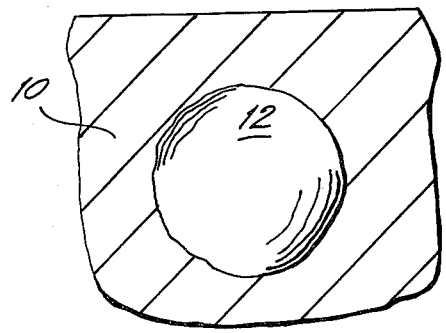
FIG. 4 is a schematic illustration of an implant of the invention situated in tissue.

In accordance with one of the methods of the present invention, an absorbable substance is injected into the interior tissue of a subject such as a human being, animal, or the like. Thus, FIG. 4 shows internal tissue 10 having a body of absorbable substance 12 according to the present invention implanted therein. This substance 12 which forms at least part of the implant shown in FIG. 4 may be a hydrogenated vegetable oil or a hydrogenated animal fat, the latter substances having the property of being solid at body temperature while at the same time they are gradually absorbed by the tissue of the body so that the implant 12 of FIG. 4 will gradually reduce in size. It is emphasized, however, that in addition to the above substances it is possible to use a substance such as cat gut which will be absorbed by the tissue. In the case of solids such as hydrogenated vegetable oil or animal fats, such solids may be made to have a melting temperature which is somewhat higher than body temperature such as a temperature on the order of 130°F. Thus, in order to provide such an implant it is only necessary to melt the substances and while it is at an elevated temperature in liquid form it is implanted, as by being injected with a suitable syringe, and while the injected substance cools to body temperature it will solidify.

An injectable substance of this latter type has a temperature which is not so much higher than the body temperature when the substance is in liquid form as to create undesirable pain when injected. However, if desired the needle of the syringe can be covered with a suitable insulating layer to insulate the tissue from the liquid hydrogenated oil or animal fat which is at elevated temperature while it is injected.

However, one of the important advantages which can be achieved with the present invention is that it is possible to disperse through the absorbable substance a suitable agent such as a drug or antibiotic having medicinal properties, so that with the present invention it becomes possible to continuously release such an agent through the tissue to the body at a predetermined steady rate. For this purpose, when a substance such as hydrogenated vegetable oil or animal fat is melted, an agent of the above type is added to the molten substance, and then such a substance can be injected in the manner described above.

Figure 5:
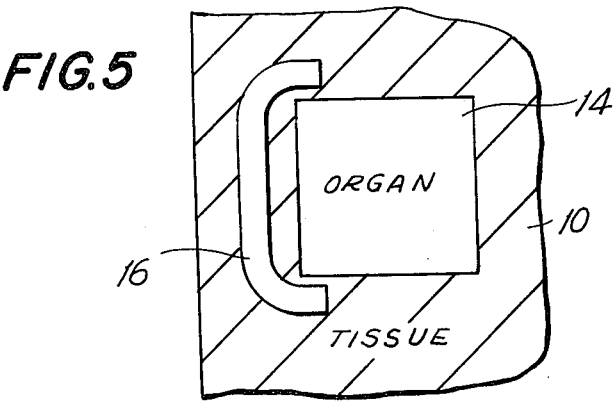
FIG. 5 is a schematic illustration of another type of implant situated in tissue.

Referring to FIG. 5, it will be seen that in the tissue 10 there is a diagrammatically illustrated organ 14 which may be any of the organs of the body. While a substance of the above type with an agent dispersed therethrough is still in liquid form, it can be injected so as to provide a casting 16 as illustrated in FIG. 5. Thus the injection can easily be carried out in such a way that the injected substance will become closely located along and around an organ 14 or the like so that the agent which is released will directly affect the organ which is intended to receive the agent without necessitating general administering of the agent throughout the body.

Instead of injecting a substance of the above type in liquid form, the substance can be heated to liquid form only for the purpose of having a desired agent of the above type added thereto, and then the substance can be solidified. This solidified substance can then be crushed into a particulate form such as the form of a suitable powder. However, in order to achieve a powder of this latter type it is preferred to spray the substance which has the agent dispersed therethrough with a suitable inert gas spray which will provide fine droplets which solidify while cooling in the inert gas to form in this highly effective manner a fine powder. The particles of such a powder will of course also be absorbable by the body and will have an agent of the above type dispersed therethrough.

Figure 1:
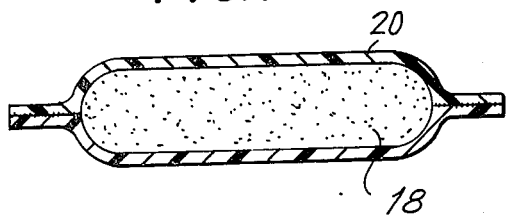
FIG. 1 is a schematic illustration of a package containing a particulate material which may form part of an implant of the invention.

As may be seen from FIG. 1, such a powder 18 may simply be situated in a suitable package 20 made of polyethylene or the like and suitably lined with a film of aluminum or the like, so that a long shelf life is assured. If desired the interior of the package may be provided with a suitable atmosphere such as an atmosphere of carbon dioxide.

When it is desired to use the particles as shown in FIG. 1, they need only be placed in a suitable liquid carrier such as a suitable saline solution or a gelatin solution. Another type of liquid hydrogenated vegetable oil or the like which is liquid at room temperature is less desirable because the solid particles will partly dissolve into the liquid substance. Thus by situating the particles 18 in a carrier in which the particles will not dissolve it is possible for these solids to remain in the body for a long period of time gradually releasing the agent to the tissue of the body. The carrier is absorbed more rapidly than the solids carried thereby, and these solids may take the form of superfine particles or it is also possible to have a liquid agent which will gradually dissolve while being carried by a suitable carrier. Such a liquid agent may be in the form of find droplets dispersed through a solid carrier.

Figure 2:
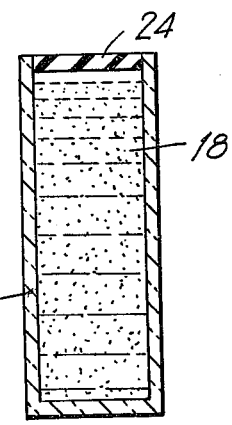
FIG. 2 is a schematic sectional elevation showing another type of container for containing implantable particulate material which is suspended in a suitable liquid carrier.

Thus, FIG. 2 shows a container 22 in the form of a suitable vial which may be closed at its top end by a rubber closure element 24. Within this vial 22 is located a carrier liquid such as a saline solution which has dispersed therethrough the particles 18. Thus, FIG. 2 shows a suitable package for the invention. With this package the needle of the syringe need only be punctured through the cover 24 so as to draw into the syringe the liquid carrier with the particles of the invention therein, and then the injection can be made at a desired location.

In connection with a particulate form of substance of the invention as described above in connection with FIGS. 1 and 2, it is to be noted that it is also possible to use a material such as cat gut for the substance of the present invention, even though this material cannot be melted in the same way as hydrogenated vegetable oil or animal fats. Such cat gut can be divided up into relatively small particles which when placed in a suitable evacuated atmosphere can have impregnated into the pores thereof an agent such as a suitable antibiotic, drug, or the like. Then these cat gut particles, which are chopped up into a fine particulate form, can be utilized in the same way as the particles 18 described above and shown in FIGS. 1 and 2.

Figure 3:
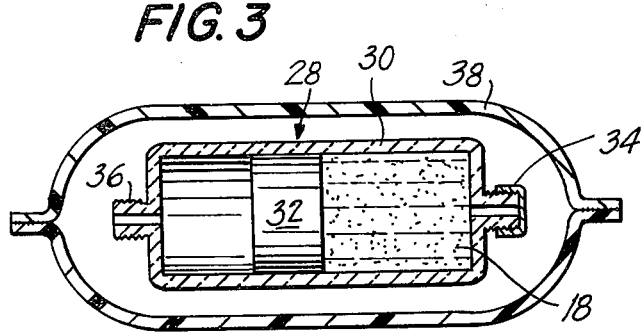
FIG. 3 is a schematic sectional elevation of part of a syringe which may be used for the implanting method of the invention.

Inasmuch as particles of the type referred to above, when suspended in a suitable liquid carrier, may be difficult to inject with a conventional syringe, it is possible according to a further feature of the invention to package the liquid carrier and the particles of the invention suspended therein in a syringe of the type shown in FIG. 3. Thus, FIG. 3 shows a syringe 28 having an elongated cylindrical barrel 30 in which a piston 32 is slidable. The barrel 30 is provided at its right end, as viewed in FIG. 3, with a threaded opening closed by a suitable cap 34 and capable of having a hollow needle attached thereto just prior to the injection of the liquid carrier and particles suspended therein, the liquid carrier and particles 18 suspended therein being housed within the syringe between the piston 32 and the cap 34 in the manner shown in FIG. 3.

The opposite end of the barrel 30 is provided with a suitable fitting 36 capable of being attached to any suitable source of air under pressure. Thus with such a syringe the air pressure will be introduced into the barrel through the fitting 36 behind the piston 32 in order to drive the latter for discharging the contents of the syringe into the body tissue. The entire syringe structure 28 can be housed within a suitable package 38 similar to the package 20 of FIG. 1.

As was pointed out above, the agents which are dispersed through the absorbable substance of the invention may be medicinal agents such as suitable drugs, antibiotics, or the like. Thus penicillin, for example, may be such an agent, and other possible agents are steroids such as cortisone, as well as anabolic steroids, estrogenic steroids, etc. Moreover, it is possible to visualize circumstances where nutrient or vitamin agents are dispersed through the absorbable substance so as to be released to the tissue of the body.

What is claimed is:

1. Method of treating a living being over a prolonged period of time with an agent which affects the health of said living being by causing said agent to be slowly released during said period of time within internal tissue of said living being, which comprises implanting in liquid molten condition a depot of a substance which solidifies in the internal tissue of said living being and which is safely absorbable by said living being, said substance solidifying at the temperature of the body of said living being and being molten and liquid at a higher temperature at which it is implanted, the implanting temperature not adversely affecting the living being during the implanting, said substance having distributed therethrough said agent which affects the health of said living being so that as said substance is absorbed by the living being the agent is released within the internal tissue of said living being to act on its health.

2. In a method as recited in claim 1 and wherein the depot is situated in internal tissue of the subject adjacent an organ for directly affecting the organ with said agent during release of the latter.

3. In a method as recited in claim 2 and wherein the molten substance containing said agent is initially injected into the tissue along the organ so that upon solidification of the substance the solid becomes located close to and extends along the organ for releasing the agent which will directly affect the organ.

4. In a method as recited in claim 1 and wherein said substance is a hydrogenated vegetable oil, animal fat, or the like.

5. In a method as recited in claim 1 and wherein said agent is an antibiotic.

6. In a method as recited in claim 1 and wherein said agent is a drug.

* * * * *